United States Patent
Amano et al.

(10) Patent No.: US 8,033,993 B2
(45) Date of Patent: Oct. 11, 2011

(54) ENDOSCOPE DEVICE AND DISPLAY DEVICE

(75) Inventors: Hirotoshi Amano, Kodaira (JP); Keiji Okada, Hachioji (JP); Katsushi Watanabe, Hachioji (JP)

(73) Assignees: Olympus Medical Systems Corp., Tokyo (JP); Olympus Imaging Corp., Tokyo (JP)

( * ) Notice: Subject to any disclaimer, the term of this patent is extended or adjusted under 35 U.S.C. 154(b) by 746 days.

(21) Appl. No.: 11/715,801

(22) Filed: Mar. 8, 2007

(65) Prior Publication Data

US 2007/0249904 A1 Oct. 25, 2007

(30) Foreign Application Priority Data

Mar. 9, 2006 (JP) ................................ 2006-063546

(51) Int. Cl.
  *A61B 1/06* (2006.01)
  *A62B 1/04* (2006.01)
(52) U.S. Cl. ........................... 600/160; 600/162; 348/65
(58) Field of Classification Search .................. 600/120, 600/131, 160, 164, 174, 185, 188; 128/200.26, 128/207.14, 207.15; 348/65; 396/287
See application file for complete search history.

(56) References Cited

U.S. PATENT DOCUMENTS

2005/0059863 A1* 3/2005 Zilch ............................ 600/188

FOREIGN PATENT DOCUMENTS

| EP | 1 300 599 A2 | 4/2003 |
| EP | 1 736 094 A1 | 12/2006 |
| JP | 1-302216 | 12/1989 |
| JP | 2005-237513 | 9/2005 |
| JP | 2006-043094 | 2/2006 |

* cited by examiner

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

An endoscope device of the invention includes: an insertion portion disposed with an observation optical system; an operation portion continuously provided to a proximal end side of the insertion portion; a display device main body provided to a proximal end side of the operation portion and disposed with a monitor portion for displaying a subject image; a rotational movement shaft for rotationally movably journaling the display device main body with respect to the operation portion; and a finger-hooking portion provided to the display device main body and for operation of rotationally moving the display device main body about a rotational movement shaft, and thus it is possible for an operator to easily orient the monitor of the display device in an easily viewable direction when operatably grasping the operation portion.

21 Claims, 8 Drawing Sheets

ENDOSCOPE DEVICE AND DISPLAY DEVICE

This application claims benefit of Japanese Application No. 2006-63546 filed on Mar. 9, 2006, the contents of which are incorporated by this reference.

BACKGROUND OF THE INVENTION

1. Field of the Invention

The present invention relates to an endoscope device which is integrated with a small display device and is suitable for portable use.

2. Description of Related Art

Endoscope devices widely used in the medical and industrial fields include an endoscope device having a display screen so that an operator can view an observation object image at hand while holding and operating the device.

For example, Japanese unexamined patent publication No. 2005-237513 discloses an endoscope device having a display screen for displaying an observation image based on an image-capturing signal from image-capturing means, and including a display device rotatable about an axis intersecting with a longitudinal direction of a grasp portion of an operation portion.

SUMMARY OF THE INVENTION

An endoscope device according to the present invention is characterized in including: an insertion portion disposed with an observation optical system; an operation portion continuously provided to a proximal end side of the insertion portion; a display device main body provided to the proximal end side of this insertion portion, the display device main body being disposed with a monitor for displaying a subject image; a rotational movement shaft for rotationally movably journaling the display device main body with respect to the operation portion; and a finger-hooking portion provided to the display device main body, the finger-hooking portion being used to operate to rotationally move the display device main body about the rotational movement shaft.

A display device of the present invention is characterized in including: a monitor; a device main body rotationally movably connected to an endoscope; and a finger-hooking portion extendedly provided to the device main body, the finger-hooking portion being for operating a rotational movement relative to the endoscope.

The above and other objects, features and advantages of the invention will become more clearly understood from the following description referring to the accompanying drawings.

DETAILED DESCRIPTION OF PREFERRED EMBODIMENT

Figure 1:
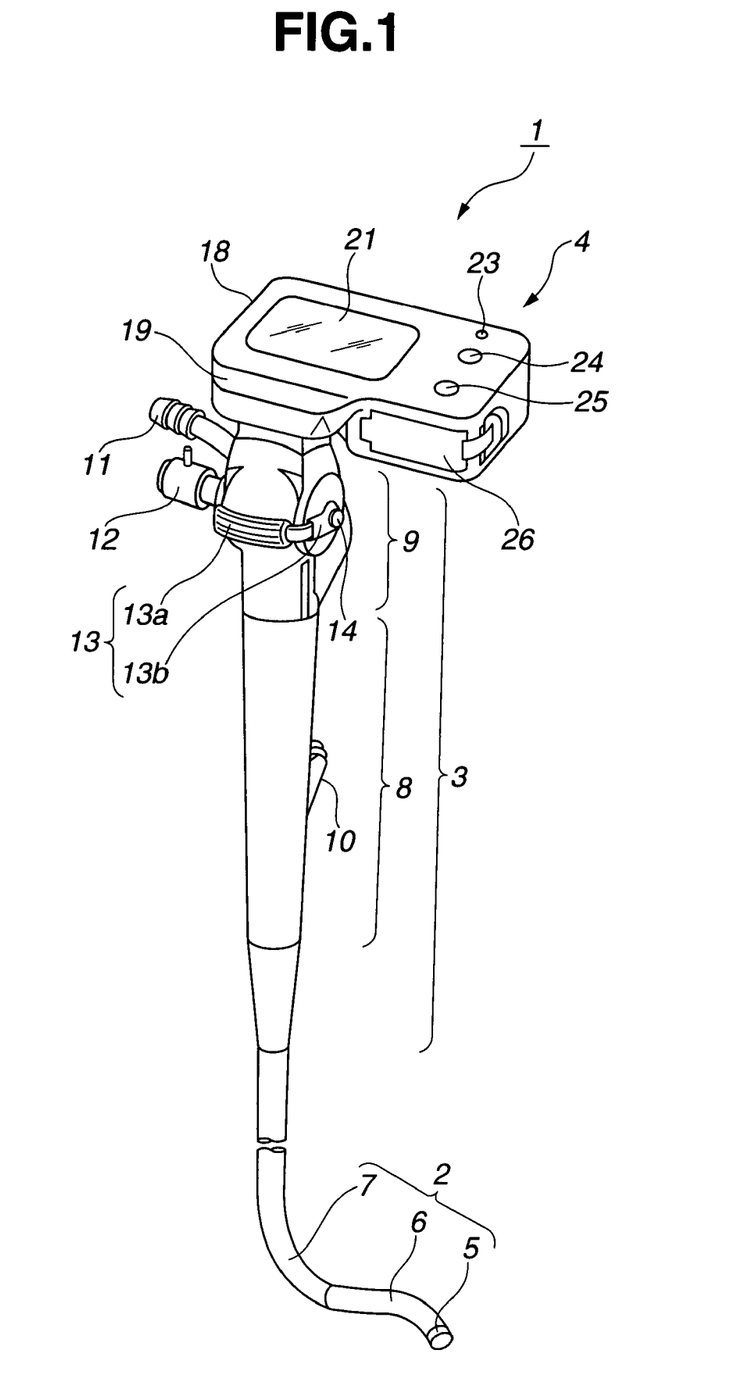
FIG. 1 is a perspective illustrative view as viewed from a rear direction of an endoscope device according to an embodiment of the present invention.
Figure 2:
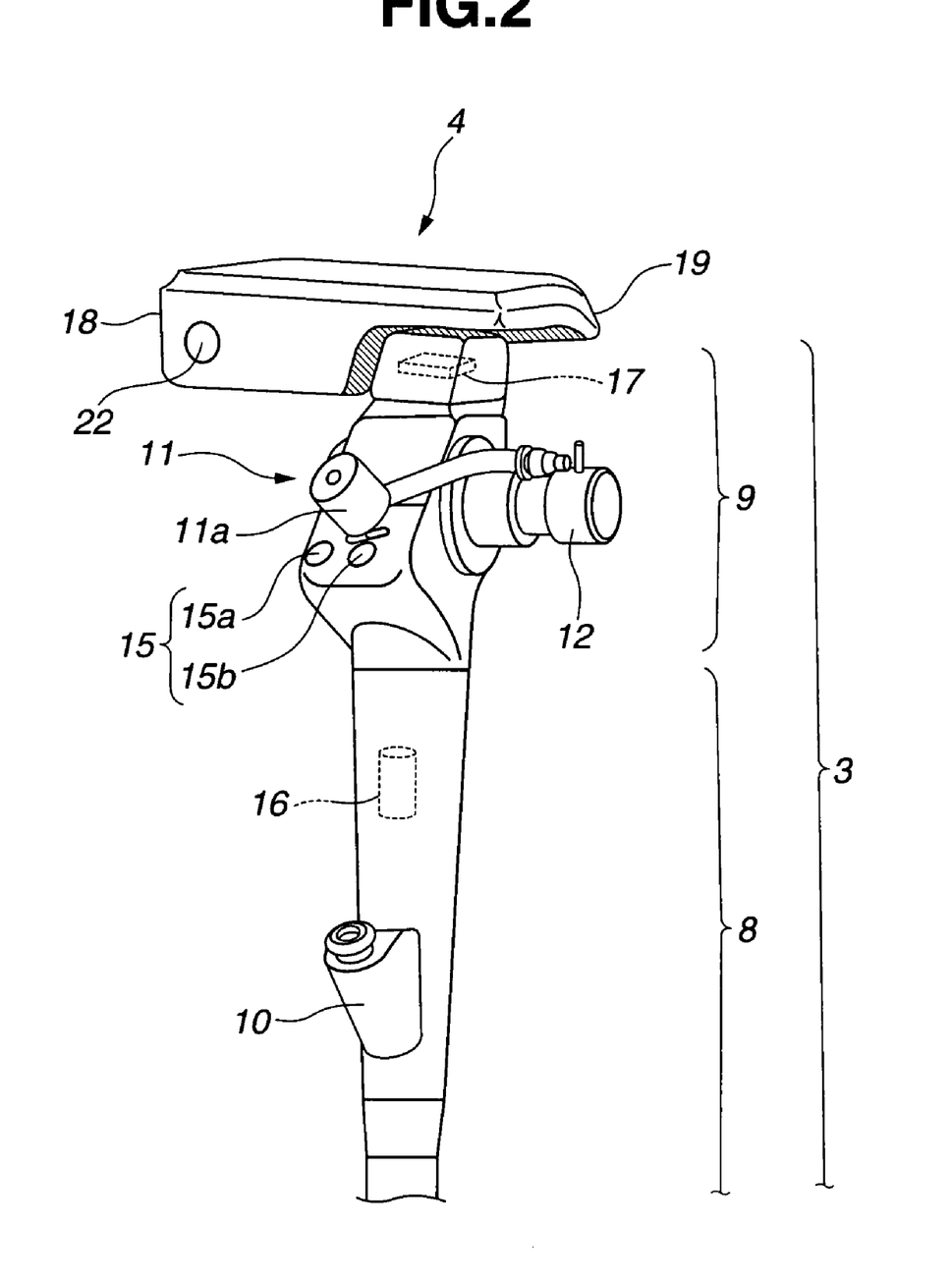
FIG. 2 is a perspective illustrative view of the endoscope device as viewed from a front direction differing from that in FIG. 1.
Figure 3:
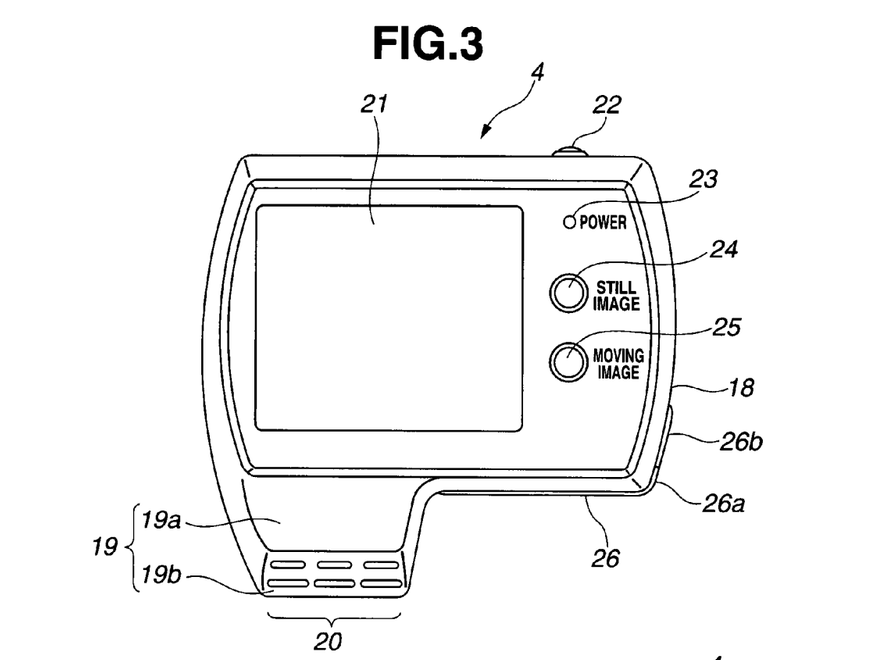
FIG. 3 is a plan view of a picture image display device as viewed from the side of a monitor.
Figure 4:
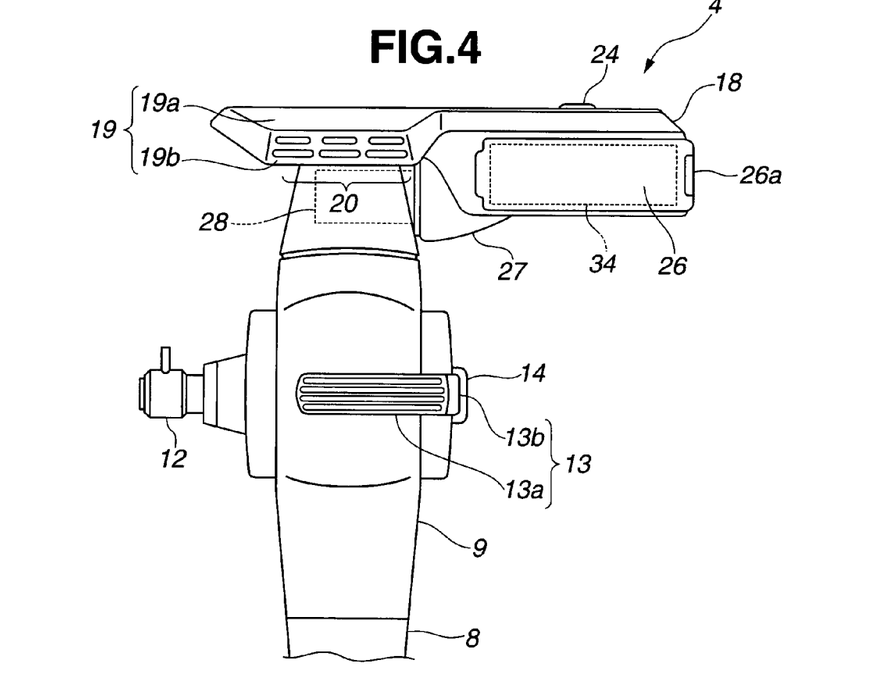
FIG. 4 is a plan view of an operation portion main body and the picture image display device when the endoscope device is viewed from the rear thereof.
Figure 5:
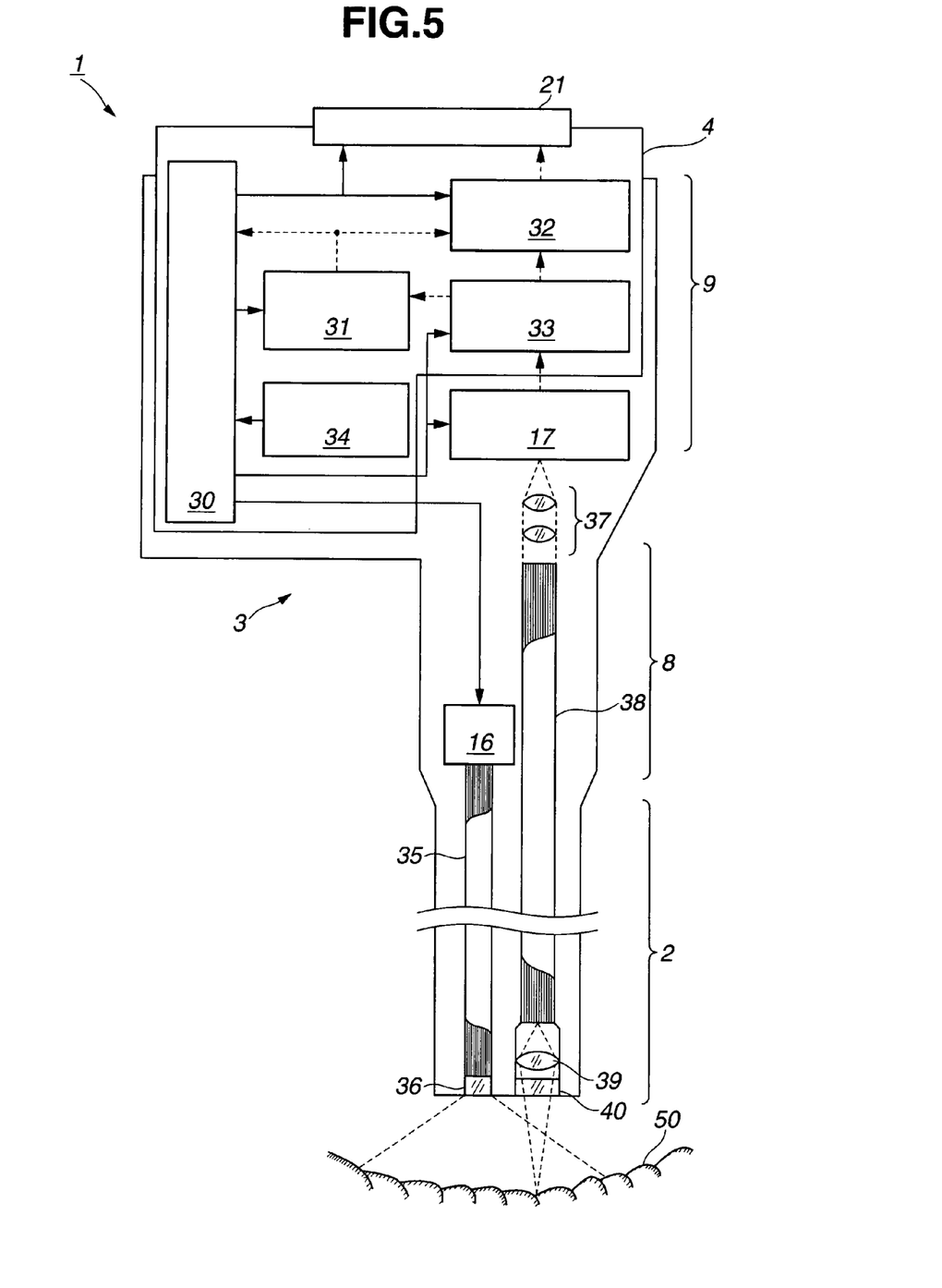
FIG. 5 is a pattern diagram to illustrate a general inner structure of the endoscope device.
Figure 6:
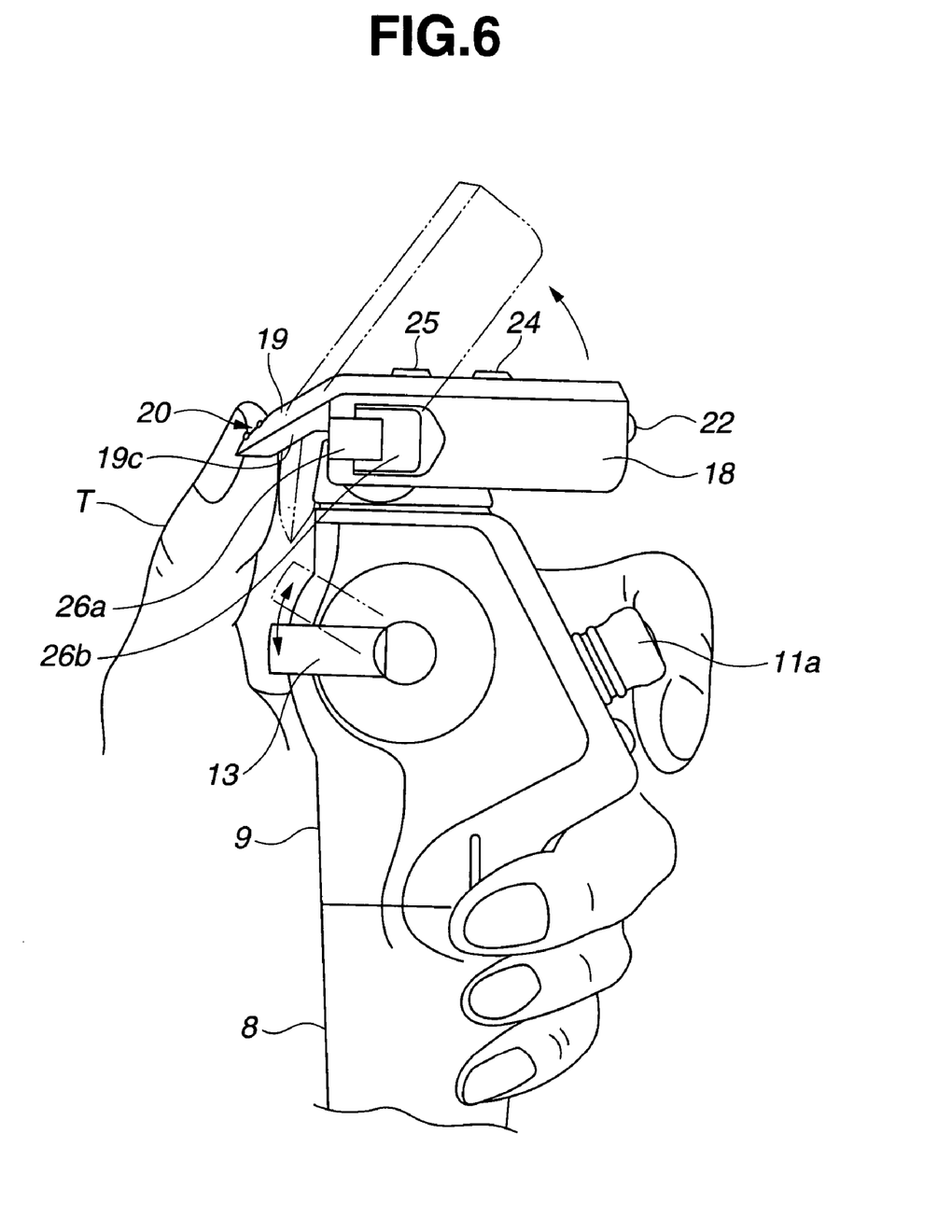
FIG. 6 is a view to illustrate an action of the picture image display device.

Referring to FIGS. 1 to 6, an endoscope device according to an embodiment of the present invention will be described below. FIGS. 1 to 6 relate to the endoscope device of the present embodiment, wherein FIG. 1 is a perspective illustrative view as viewed from the rear of the endoscope device for description thereof; FIG. 2 is a perspective illustrative view of the endoscope device as viewed from a front direction different from that in FIG. 1; FIG. 3 is a plan view of a picture image display device as viewed from the side of a monitor; FIG. 4 is a plan view of an operation portion main body and the picture image display device when the endoscope device is viewed from the rear thereof; FIG. 5 is a pattern diagram to illustrate a general inner structure of the endoscope device; and FIG. 6 is a view to illustrate an action of the picture image display device.

As shown in FIG. 1, the endoscope device 1 of the present embodiment includes an insertion portion 2 with an distal end to be inserted toward an observation region; an operation portion 3 that is continuously provided to a proximal end of the insertion portion 2 and is for operation of bending the distal end of the insertion portion 2; and a picture image display device 4 disposed at a top end of the operation portion 3.

The insertion portion 2 has an elongate flexible shape, is connected to a distal end of the operation portion 3, and includes a rigid distal end portion 5 positioned on a distal end side, a bending portion 6 continuously provided to the distal end portion 5, and a flexible portion 7 continuously provided to the bending portion 6 and having a proximal end side connected to the operation portion 3.

The operation portion 3 includes a grasp portion 8 to be used by an operator to grasp the endoscope device 1; and an operation portion main body 9 provided at a proximal end of the grasp portion 8.

The grasp portion 8 is rod-like and formed in a shape that can be grasped and covered by the thumb and the other fingers. To this end, the grasp portion 8 has a longitudinal direction provided to cause fingers except the thumb to be adjacently disposed when the operator grasps the grasp portion 8 with a hand. In a halfway portion of the grasp portion 8, there is disposed a forceps insertion opening 10 from which to insert a treatment tool such as a forceps.

The operation portion main body 9 includes a suction connector 11 for sucking a liquid such as a body fluid; a venting connector 12 for feeding air to the inside of the endoscope device 1 in a water leak test thereof; and a bending operation lever 13 for bending the bending portion 6 in a desired direction via operation wires not shown introduced in the insertion portion 2.

The suction connector 11 is connected with a suction device via a tube not shown. The operator can operate to suck the body fluid or the like through the suction connector 11 (see FIG. 2) by activating the suction device and operating a suction button 11a.

The venting connector 12 is connected with an air supply device via a tube not shown. The operator can conduct the water leak test for the inside of the endoscope device 1 by activating the air supply device to feed air into the inside of the endoscope device 1 from the venting connector 12.

The bending operation lever 13 serving as a bending operation portion is provided adjacent to the grasp portion 8 so that the operator can operate the lever with the thumb of the hand grasping the grasp portion 8. The bending operation lever 13 is L-shaped, including a finger-hooking portion 13a serving as a bending operation portion which is positioned at the rear of the operation portion main body 9 and is operated by the operator with the belly of the thumb of the hand grasping the grasp portion 8; and a proximal end portion 13b communicating with one end of the finger-hooking portion 13a.

The bending operation lever 13 is rotationally movably supported by a shaft 14 serving as an operation-portion-side rotational movement shaft provided to the operation portion main body 9, with the proximal end portion 13b being journaled on the shaft 14 at an approximate center on a side surface of the operation portion main body 9, i.e. a right side surface as viewed on the page surface of FIG. 1. The bending operation lever 13 is constituted to allow for bidirectional free bending of the bending portion 6 through pushing up and pulling down the finger-hooking portion 13a with the thumb so as to apply a tensional force to one of the wires.

As shown in FIG. 2, the operation portion 3 is also provided, on a front surface side thereof, with image switches 15 including an image recording switch 15a for recording a picture image being displayed on the picture image display device 4 in an image recording device to be described later; and an image reproduction switch 15b for reproducing the recorded image.

Also disposed on the front surface of the operation portion main body 9 is the suction button 11a constituting a root portion of the suction connector 11 described above.

Note that, the endoscope device 1 of the present embodiment includes a white LED unit 16 serving as a light source which is built in the grasp portion 8, and an image capturing element 17, such as a CCD and a CMOS, serving as an image capturing means built in the operation portion main body 9, as described below.

Next, referring to FIGS. 3 and 4, the picture image display device 4 of the present embodiment is described.

As shown in FIGS. 3 and 4, the picture image display device 4 of the present embodiment has an exterior shape formed by a display device main body (hereinafter abbreviated simply as "device main body") 18 having a generally rectangular parallelepiped shape of a box shape; and a tilt angle varying lever (hereinafter abbreviated simply as "tilt lever") 19 serving as a finger-hooking portion extended to form a plane from one edge corner portion of the device main body 18.

Disposed on a top surface of the device main body 18 are a monitor portion 21 which is a display element (LCD: Liquid Crystal Display) for displaying an endoscope image; a POWER display lamp 23 that lights on when the power is turned on; a still-image recording switching switch 24 for setting the endoscope image for recording to a still-image; and a moving-image recording switching switch 25 for setting the endoscope image for recording to a moving-image.

Further, disposed on one side surface of the display device main body 18 is a power source switch (activation switch) 22. On another side surface opposing to the one side surface on which the power source switch 22 is provided, there is disposed an openable and closable lid body 26 used when housing and removing a battery 34 and a memory medium, such as a memory card not shown, to and from a housing portion (not shown) in the device.

These components disposed to the display device main body 18 each have a watertightness-maintaining structure. Especially, the opening and closing lid body 26 includes a fixing nail 26a and a buckle lever 26b constituted to ensure the watertightness-maintaining structure of the display device main body 18.

The monitor portion 21 of the above-mentioned picture image display device 4 is provided so as to externally expose a display screen for rendering a subject observation image to a picture image and displaying the picture image.

The tilt lever 19 serving as a finger-hooking portion is extended from the one side surface side of the device main body 18 to allow for operation by an operator with the belly of the thumb grasping the grasp portion 8. The tilt lever 19 of the present embodiment includes an extended plane portion 19a which is a protruding surface tilted with respect to an extending direction toward the side of the operation portion main body 9; and a finger-hooking plane portion 19b which is a finger-hooking surface further tilted toward the side of the operation portion main body 9 continuously from an extended end edge of the extended plane portion 19a. Moreover, in consideration of operatability for the operator, width dimension of the finger-hooking plane portion 19b in a transverse direction thereof is set to have a predetermined dimension wider than that of a thumb of a typical adult, and further includes anti-slips 20 which is a plurality of convex portions formed on the surface of the plane.

In the endoscope device 1 of the present embodiment, the tilt lever 19 is provided to protrude closer to the hand side of the operator than the finger-hooking portion 13a serving as a bending operation portion. With this, the endoscope device 1 prevents the operator from making an erroneous bending operation by accidentally touching the finger-hooking portion 13a when operating the tilt lever 19.

In addition, the finger-hooking plane portion 19b of the tilt lever 19 and the finger-hooking portion 13a of the bending operation lever 13 each have a surface generally parallel to respective rotational movement shaft, as viewed by the operator from the rear direction of the operation portion main body 9, and extend to have the above-mentioned predetermined dimension over both left and right directions interposing therebetween a center axis of the operation portion main body 9 in a longitudinal direction thereof. Thus, the finger-hooking plane portion 19b and the finger-hooking portion 13a are set to prevent the operator from having a sense of discomfort in the operatability of the levers 13, 19, regardless of whether the operator grasps the grasp portion 8 with left or right hand.

The suction button 11a, and the image recording and reproduction switches 15a, 15b disposed on the front surface of the operation portion main body 9 are present in an area permitting for operation by the operator with the forefinger of a hand grasping the grasp portion 8. Therefore, with the endoscope device 1 of the present embodiment, all the operations, including the above-mentioned operations of the levers 13, 19, can be performed with only one hand.

The picture image display device 4 of the present embodiment thus constituted is disposed so that the tilt lever 19 is positioned near the top of the operation portion main body 9, as shown in FIG. 4. Specifically, the picture image display device 4 has, on a rear side thereof, a tilting rotation portion 27 from which a rotational movement shaft 28 is extendedly provided. The rotational movement shaft 28 provided extendingly from the tilting rotation portion 27 is journaled in the operation portion main body 9 and is thus disposed to be rotationally movable with respect thereto.

The rotational movement shaft 28 is journaled in the operation portion main body 9 with a predetermined resistance, thereby preventing a rotational movement of the picture image display device 4 due to self-weight or the like. That is, the rotational movement shaft 28 is applied with a predetermined resistance so that, when the operator applies an operational pressure to the tilt lever 19 to operate to rotationally move the picture image display device 4 about the rotational movement shaft 28 and determines a desired angle of the display device 4 with respect to the operation portion main body 9, the picture image display device 4 stays still at that position.

Moreover, the rotational movement shaft 28 is generally parallel to the shaft 14 on which is journaled the bending operation lever 13 disposed to the operation portion main body 9. In other words, the bending operation lever 13 and the picture image display device 4 share a common rotational movement operational direction with respect to the operation portion main body 9.

Note that protrusion amount of the tilt lever 19 is set to prevent interference between the tilt lever 19 and the bending operation lever 13 in an operating range thereof. Specifically, the protrusion amount of the tilt lever 19 is set to prevent interference and thus contact between the position of the tilt lever 19 when the picture image display device 4 is operated to rotationally move to the limit toward the side of the operation portion main body 9 (downward side), and the position of the finger-hooking portion 13a when the bending operation lever 13 is operated to rotationally move to the limit toward the side of the picture image display device 4 (upward side), as shown in FIG. 6.

The finger-hooking portion 13a of the bending operation lever 13 is disposed on a predetermined side surface side of the operation portion main body 9, and is disposed on a downward side in FIG. 6, i.e., closer to the tip-end side of the endoscope device 1 than the finger-hooking plane portion 19b of the tilt lever 19 protruding in the same direction on the side surface side. Also, an operational plane, on which to hook a finger, of the finger-hooking portion 13a of the bending operation lever 13, and the finger-hooking plane portion 19b of the tilt lever 19 are planes that are constantly generally parallel to the respectively corresponding shafts 14, 28 about respective circumferences of the shafts 14, 28.

Now, referring to FIG. 5, an internal configuration of the endoscope device 1 is described.

Built in the picture image display device 4 of the endoscope device 1, besides the above-mentioned monitor portion 21 and the battery 34, are a power supply control circuit 30, a recording control circuit 31, a display element control circuit 32, and an image-capturing element control circuit 33.

Furthermore, inserted across from the insertion portion 2 of the endoscope device 1 to the grasp portion 8 of the operation portion 3 are a light guide (illumination light guiding means) 35 serving as an illumination optical system, and an image guide (observation image capturing portion) 38 which is an observation optical system.

An illumination light from the white LED unit 16 which is an illumination member provided in the above-mentioned grasp portion 8 is emitted on one end surface of the light guide 35 positioned in the grasp portion 8, is introduced through the light guide 35, and then is externally emitted from the other end surface of the light guide 35 on the side of the insertion portion 2. At this time, the illumination light is emitted toward a subject 50 such as body cavity tissues in a predetermined range, via an illumination lens 36 which is an illumination optical system provided in the distal end portion 5 (see FIG. 1) and is an illumination window.

In the operation portion main body 9 is provided a light collecting lens 37 for forming an image (light) from one end surface of the image guide 38 on the image capturing element 17. The other end surface of the image guide 38 is positioned at the distal end portion 5 of the insertion portion 2, and constitutes an optical member disposed on a distal end side thereof. On the other end surface is formed an image by a reflection light from the subject illuminated by the illumination light, via an image-capturing lens 40 serving as an image-capturing window, and an objective lens 39 which is one of the observation optical systems.

That is, the image by the reflection light from the subject is introduced through the image guide 38 via the image-capturing lens 40 and the objective lens 39, and is subsequently formed on the image capturing element 17 via the light collecting lens 37. Note that the endoscope device 1 may not include the image guide 38, and be of a type having image capturing element 17 built in the distal end portion 5. Also note that a light path for the image reaching from the image guide 38 to the image capturing element 17 may be folded by a mirror surface member as needed, although in the present embodiment, the light collecting lens 37 and the image capturing element 17 are placed on the optical axis of the image.

The power supply control circuit 30 of the picture image display device 4 uses an electric power supplied from the battery 34 to output driving electric powers respectively corresponding to the white LED unit 16, the image capturing element 17, the monitor portion 21, the recording control circuit 31, the display element control circuit 32, and the image-capturing element control circuit 33. The power supply control circuit 30 includes the above-mentioned power source switch 22 which turns ON/OFF the power. Note that the battery 34 is a secondary battery capable of repeated charging and use.

The image of the subject 50 formed by the light collecting lens 37 is outputted from the image capturing element 17 to the image-capturing element control circuit 33. The image-capturing element control circuit 33 renders the image captured by the image capturing element 17 into a signal, and then outputs the signal to the recording control circuit 31 and the display element control circuit 32.

To the recording control circuit 31, a recording medium such as an XD picture card can be detachably attached. The recording control circuit 31 is supplied with signals from the image switches 15 (the image recording switch 15a and the image reproduction switch 15b) provided to the operation portion main body 9 of the endoscope device 1, the still-image recording switching switch 24 and the moving-image recording switching switch 25 of the picture image display device 4.

In response to these various signals, the recording control circuit 31 performs controls of still- or moving-image recording, reproduction, pause, or the like, of an endoscope image signal. That is, the recording control circuit 31 stores, in the recording medium, the image of the subject 50 rendered into a signal from the image-capturing element control circuit 33, and then outputs the stored signal to the display element control circuit 32 in response to an instruction for reproduction, pause or the like, by the image reproduction switch 15b.

The display element control circuit 32 renders a signal from the recording control circuit 31 or the image-capturing element control circuit 33 into a picture image, and displays an endoscope image on the monitor portion 21. The recording control circuit 31 supplies to the power supply control circuit 30 an instruction signal for supplying an electric power to the white LED unit 16, the image capturing element 17, and the image-capturing element control circuit 33 to be driven in response to the various switches.

When the power source switch 22 is turned on, the power supply control circuit 30 of the picture image display device 4 supplies an electric power to the white LED unit 16 for emitting illumination light; the monitor portion 21, the display element control circuit 32, and the image-capturing element control circuit 33 of the picture image display device 4; and the image capturing element 17 of the operation portion main body 9. This starts up an image display function constituted from these units, thus converting the endoscope device 1 constituted as described above into an activation state.

An image under observation (Live View) presents an image real-time via from the image capturing element 17 through the path of the image-capturing element control circuit 33, the display element control circuit 32, and the monitor portion 21.

For instance, in the case of recording a still-image, the operator pushes the still-image recording switching switch 24 to obtain a still-image recording wait state. Subsequently, on pushing the image recording switch 15a, an image signal is captured into the recording control circuit 31 from the image-capturing element control circuit 33, and then recorded in the internal memory. Note that, after the recording, the device automatically returns to the above-mentioned Live View state.

Then, when the operator pushes the image reproduction switch 15b, the image signal is outputted from the recording control circuit 31 to the display element control circuit 32, thereby displaying the recorded still-image on the monitor portion 21.

When the operator again pushes the image reproduction switch 15b to end the image reproduction, the device returns to the above-mentioned activation state.

Furthermore, in the case of recording a moving-image, the operator pushes the moving-image recording switching switch 25 to obtain a moving-image recording wait state. Then, when the operator pushes the image recording switch 15a, the moving-image is recorded in the internal memory, likewise with the description above.

During the moving-image recording, either the image-capturing element control circuit 33 or the recording control circuit 31 outputs the image signal, real-time, to the display element control circuit 32 to display the through image being recorded on the monitor portion 21.

Moreover, when the operator again pushes the image recording switch 15a, the recording stops and the device returns to the initial state. In the case of subsequently reproducing the moving image, when the operator pushes the image reproduction switch 15b, a control similar to the still-image reproduction is performed. Note that in this case, each push of the image reproduction switch 15b may result in sequential switchings of a moving-image initial screen, starting of the moving-image reproduction, and ending of the moving-image reproduction. When ending the moving-image reproduction, a control similar to the ending of the still-image reproduction is performed, which is followed by the returning to the above-mentioned activation state.

Here, referring mainly to FIG. 6, there is described an action of operating to rotationally move the picture image display device 4 of the endoscope device 1 with respect to the operation portion main body 9.

In the present embodiment, the picture image display device 4 is rotationally movably disposed to the operation portion main body 9 via the rotational movement shaft 28 (see FIG. 4) of the tilting rotation portion 27. Therefore, for example, when holding the endoscope device 1 as shown in FIG. 6, the operator can freely vary the angle of the picture image display device 4 with respect to the operation portion main body 9.

In the operation of rotationally moving the picture image display device 4 about the rotational movement shaft 28, the operator can change the position of the picture image display device 4 to face straight the monitor portion 21, by pushing up and down the tilt lever 19 of the picture image display device 4 with the thumb of the hand grasping the operation portion 3.

That is, by pushing down the tilt lever 19, the operator can tilt upward the monitor portion 21 of the picture image display device 4 in a direction of raising a backside of the monitor portion 21 as viewed from the operator, while by pushing up the tilt lever 19, tilt the monitor portion 21 frontward. Note that it is not necessarily required to tilt the monitor portion 21 to face the operator straight, as long as the operator can have an easy view of the screen.

Also note that, even if the operator once determines the angle of the picture image display device 4 with respect to the operation portion main body 9, to an easily viewable desired angular position, such as that of facing the monitor portion 21 straight, and then releases the thumb from the tilt lever 19, the angle of the picture image display device 4 with respect to the operation portion main body 9 is retained constant, since the rotational movement shaft 28 in the operation portion main body 9 is applied with the predetermined resistance.

The picture image display device 4 is configured to enable the operator to easily perform, out of these operations, the operation of tilting upward the monitor portion 21 of the picture image display device 4 in a direction of raising the backside of the monitor portion 21 as viewed from the operator, in that the extended plane portion 19a of the tilt lever 19 is tilted downward by a predetermined angle with respect to the top surface of the device main body 18 arranged with the monitor portion 21; that the finger-hooking plane portion 19b is tilted further downward by a predetermined angle than the extended plane portion 19a; and that the finger-hooking plane portion 19b is provided with the anti-slips 20 which are plurality of convex portions.

Moreover, a back surface portion 19c of the tilt lever 19 (see FIG. 6) contacts the top end portion of the operation portion (in which the rotational movement shaft 28 is housed), thereby restricting a downward rotational movement of the tilt lever 19, that is, restricting the device main body 18 from rising up. To this end, the tilt lever 19 is prevented from entering an rotational movement range of the bending operation lever 13. This prevents interference between the tilt lever 19 and the bending operation lever 13 even when the tilt lever 19 is pushed down to the maximum and the bending operation portion is pushed up to the maximum, thus providing a good operatability.

As described above, the endoscope device 1 of the present embodiment is constituted to achieve operatability significantly improved compared to a conventional device, allowing the operator to perform various operations along with operating the bending operation lever 13, with only the one hand grasping the operation portion 3, in that the operator can change the orientation of the monitor portion 21 of the picture image display device 4 in a desired, i.e. easily viewable direction with only one hand grasping the operation portion 3, and that the suction button 11a, and the image recording switch 15a and the image reproduction switch 15b are present in an area where operations thereof can be performed with the one hand.

Next, referring to FIGS. 7 to 11, a first modification example of the present embodiment is described.

Figure 7:
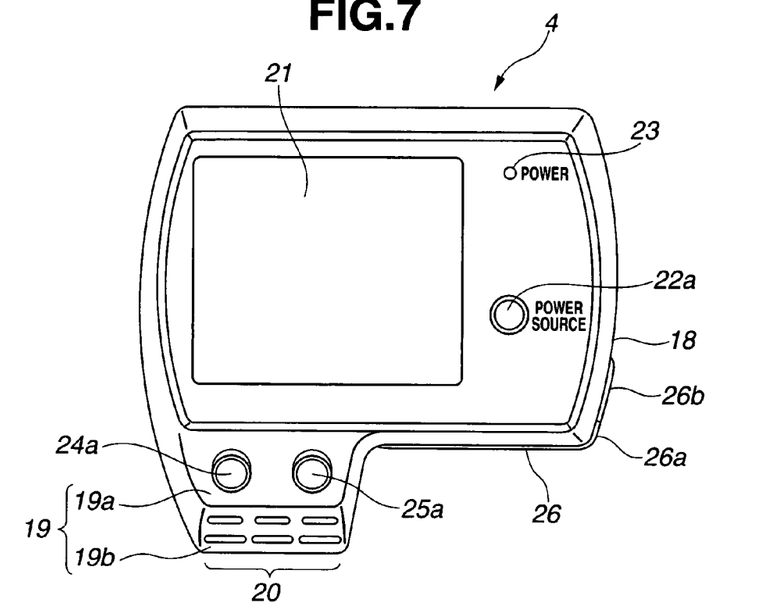
FIG. 7 is a plan view of a picture image display device of a first modification example of the present embodiment, as viewed from the side of the monitor.
Figure 8:
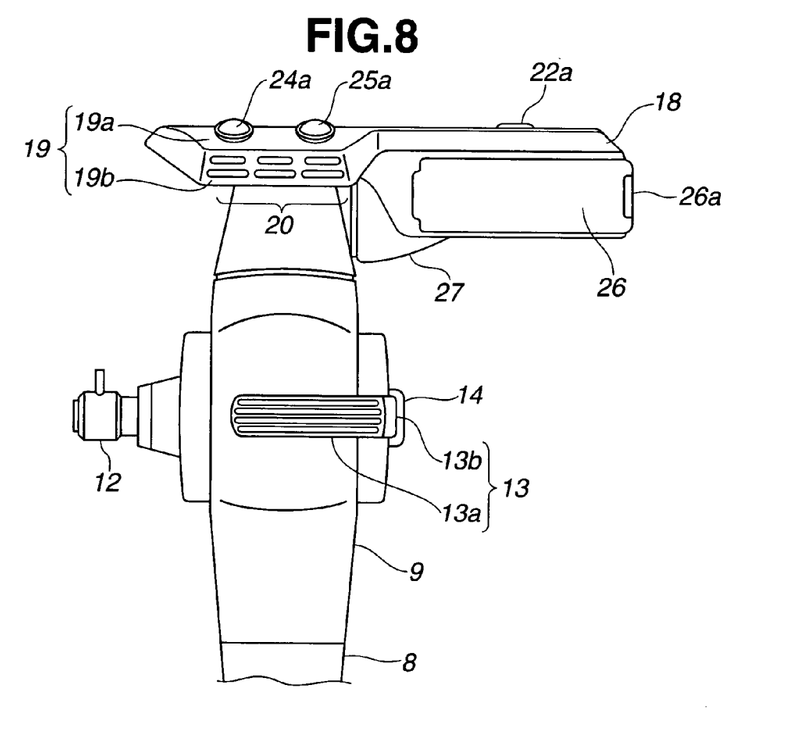
FIG. 8 is a plan view of the operation portion main body and the picture image display device when the endoscope device is viewed from the rear thereof.
Figure 9:
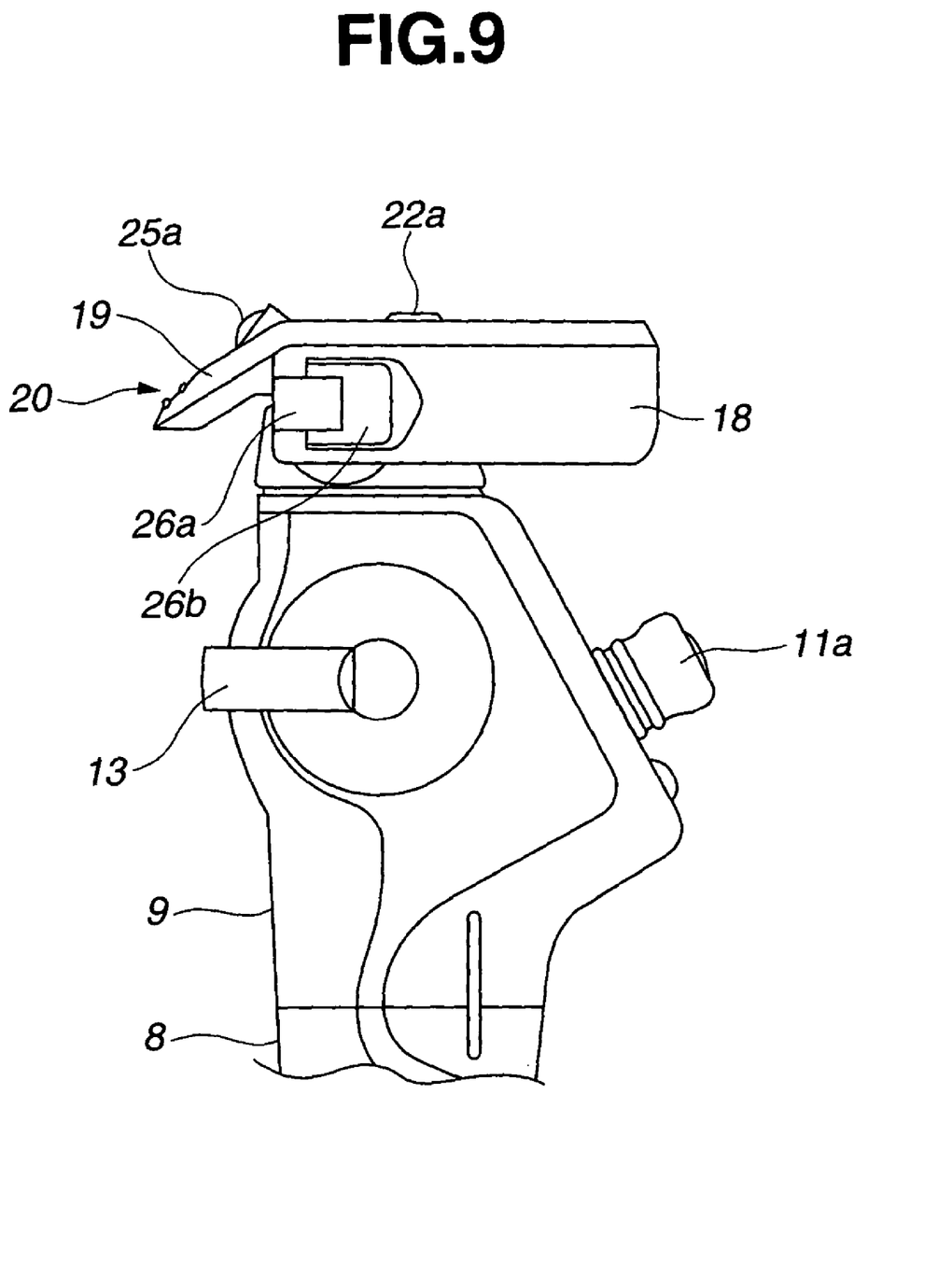
FIG. 9 is a plan view of the picture image display device and the operation portion as viewed from one side thereof.
Figure 10:
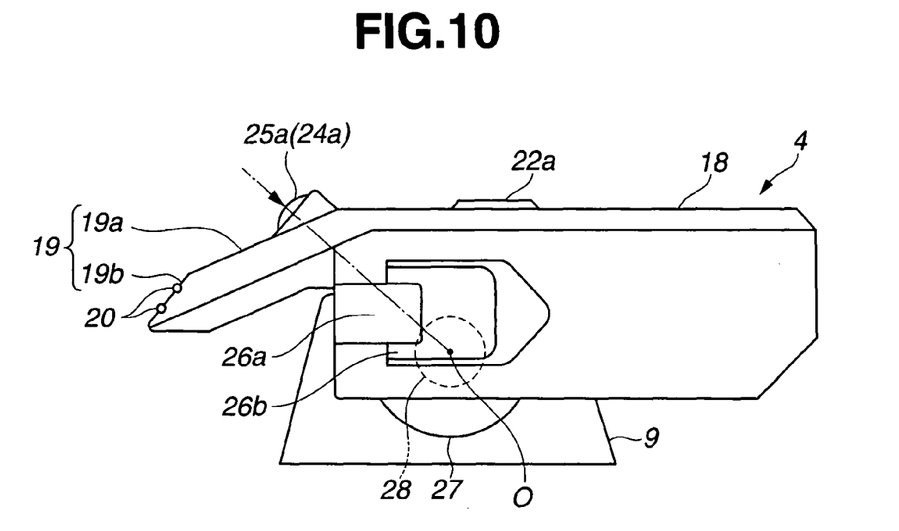
FIG. 10 is a view to illustrate an action of the picture image display device of the first modification example.
Figure 11:
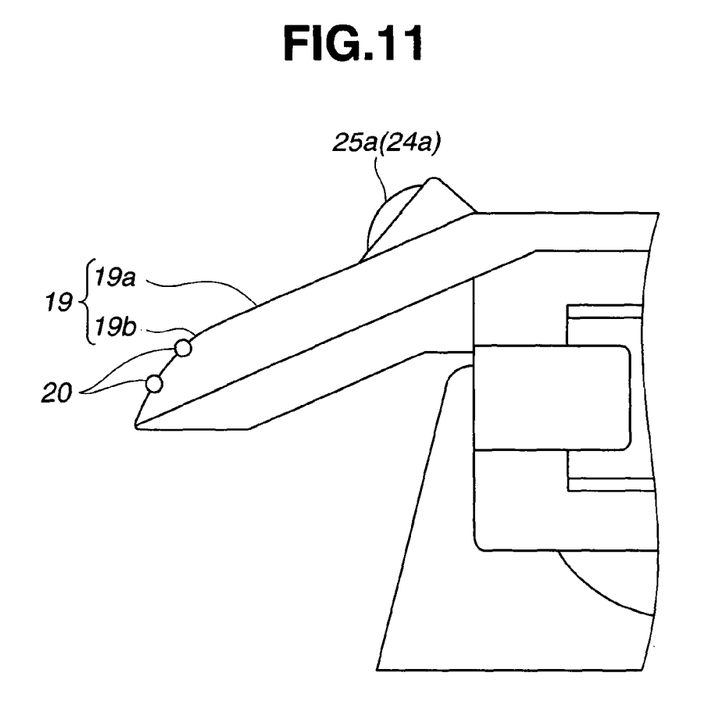
FIG. 11 is an expanded view of a tilt angle varying lever as viewed from one side thereof, according to the first modification example.

FIGS. 7 to 11 relate to the first modification example of the present embodiment, wherein FIG. 7 is a plan view of the picture image display device as viewed from the monitor side; FIG. 8 is a plan view of the operation portion main body and the picture image display device when the endoscope device is viewed from the rear thereof; FIG. 9 is a plan view of the picture image display device and the operation portion as viewed from one side thereof; FIG. 10 is a view to illustrate an action of the picture image display device of the present modification example; and FIG. 11 is an expanded view of the tilt lever as viewed from one side thereof.

As shown in FIG. 7, in the case of the picture image display device 4 of the present modification example, a power source switch 22a is disposed on the top surface of the device main body 18, and a still-image recording switching switch 24a and a moving-image recording switching switch 25a are parallelly provided on the extended plane portion 19a of the tilt lever 19.

As shown in FIGS. 8 and 9, the still-image recording switching switch 24a and the moving-image recording switching switch 25a are disposed to orient respective operation buttons thereof in an extending direction of the tilt lever 19 on the extended plane portion 19a tilted in a predetermined angle.

Also, as shown in FIG. 10, the respective operation buttons of the still-image recording switching switch 24a and the moving-image recording switching switch 25a have an operational direction that is set to validate respective switching functions with a pushing operation in a direction toward an axial center O (arrow direction in the drawing) of the rotational movement shaft 28 that is fixed to the above-mentioned tilting rotation portion 27 of the picture image display device 4 and is journaled by the operation portion main body 9.

In other words, the switches each have a surface with an angular setting to constantly orient the pressing direction of the switches 24a, 25a in the direction toward the center O of the rotational movement shaft 28. That is, in any tilting angle of the picture image display device 4, the direction of the force caused by pushing the switches 24a, 25a is oriented toward the center of the rotational movement shaft 28.

This prevents the pressing force applied to the tilt lever 19 in the operation of the switches 24a, 25a from resulting in an application of force of rotationally moving the picture image display device 4 at the fulcrum of the rotational movement shaft 28 due to the so-called principle of leverage. Accordingly, it is prevented that the operator unintentionally rotates the picture image display device 4 when operating the switches 24a, 25a.

The switches 24a, 25a are disposed at generally symmetrical positions relative to the center axis of the operation portion 3 to be adaptable for use with either left or right hand of the operator.

As described above, the endoscope device 1 of the present modification is constituted to enable the operator to selectively operate the recording of a still or moving endoscope image only through one-hand operation, by providing the still-image recording switching switch 24a and the moving-image recording switching switch 25a on the extended plane portion 19a of the tilt lever 19.

Note also that the finger-hooking plane portion 19b of the tilt lever 19 may be formed with a curved surface as shown in FIG. 11. This gives the operator an improved sense of fit for, e.g. the thumb hooked on the finger-hooking plane portion 19b of the tilt lever 19 to operate to rotationally move the picture image display device 4.

Note further that the picture image display device 4 may be constituted to be detachably attached to the operation portion 3.

Having described the preferred embodiment of the invention referring to the accompanying drawings, it should be understood that the present invention is not limited to the precise embodiment and various changes and modifications thereof could be made by one skilled in the art without departing from the spirit or scope of the invention as defined in the appended claims.

What is claimed is:

1. An endoscope device comprising:
   an insertion portion disposed with an observation optical system;
   an operation portion continuously provided to a proximal end side of the insertion portion;
   a display device main body provided to the proximal end side of the operation portion, the display device main body being disposed with a monitor for displaying a subject image;
   a rotational movement shaft for rotationally movably journaling the display device main body with respect to the operation portion;
   a concave portion having an opening only on one side surface near a top of the operation portion, the rotational movement shaft being inserted and disposed into the opening so as to rotate about the rotational movement shaft and maintain an angle with respect to the operation portion of the display device main body with a predetermined resistance; and
   a tilt lever including a protruding surface which is formed continuously from a surface of the display device main body, the monitor being disposed on the surface and the lever being extended from one side of the surface and provided so as to be extended from a side surface of the display device main body and adapted to rotationally move the display device main body about the rotational movement shaft by being pushed up and down with a thumb of a hand of a user who grasps the operation portion, and to vary a position of the monitor of the display device main body to a desired angled position which faces the user straight.

2. The endoscope device according to claim 1, wherein the insertion portion comprises a bending portion that is bendable in a predetermined direction.

3. The endoscope device according to according to claim 2, wherein the bending portion is operated with a bending operation portion provided on a predetermined side-surface side of the operation portion and on a side closer to the insertion portion than the tilt lever, the bending operation portion being rotationally movable about a shaft that is generally parallel to the rotational movement shaft.

4. The endoscope device according to claim 3, wherein the tilt lever and the bending operation portion are disposed at positions that prevent mutual interference therebetween in respective rotational movement range.

5. The endoscope device according to claim 4, wherein a back surface of the tilt lever configures a contact portion that comes in contact with the operation portion when the display device main body is rotationally moved to a raised position thereof, and the contact portion contacts the operation portion, thereby restricting an angle of the monitor of the display device main body when the monitor is raised to face the user straight.

6. The endoscope device according to claim 1, wherein the tilt lever has a predetermined dimension in both left and right directions sandwiching a center axis in a longitudinal direction of the operation portion.

7. The endoscope device according to claim 1, wherein the tilt lever is provided with a switch for performing a functional operation of the display device main body.

8. The endoscope device according to claim 7, wherein the switch is disposed at a position that causes a direction of pressing operation of the switch to intersect with a center of the rotational movement shaft.

9. The endoscope device according to claim 1, wherein the endoscope device comprises a housing portion in which to house a battery for supplying an electric power at least to the monitor.

10. The endoscope device according to claim 9, wherein the housing portion is provided to the display device main body.

11. The endoscope device according to claim 1, wherein the protruding surface is formed by a plane surface.

12. The endoscope device according to claim 1, wherein the protruding surface is formed by a curved surface along an extending direction.

13. The endoscope device according to claim 1, wherein the protruding surface is formed by a plurality of surfaces.

14. The endoscope device according to claim 1, wherein
the tilt lever includes a finger-hooking surface on which a user hooks a finger to operate to rotationally move the device main body, the finger-hooking surface being disposed continuously from the protruding surface; and
the finger-hooking surface includes a plurality of convex portions.

15. The endoscope device according to claim 1, wherein the insertion portion comprises a bending portion that is bendable in a predetermined direction and the tilt lever is disposed to protrude farther than the bending operation portion relative to the operation portion.

16. A display device comprising:
a device main body which is rotationally movably journaled with respect to an operation portion of an endoscope by a rotation movement shaft and which includes a monitor for displaying a subject image; wherein
the rotational movement shaft is inserted and disposed into an opening of a concave portion on only one side surface near a top of the operation portion so as to rotate about the rotational movement shaft and maintain an angle with respect to the operation portion of the display device main body with a predetermined resistance, and
the display device further comprises a tilt lever including a protruding surface which is formed continuously from a surface of the device main body, the monitor being disposed on the surface and the tilt lever being extended from one side of the surface and provided so as to be extended from a side surface of the device main body, and adapted to rotationally move the device main body about the rotational movement shaft by being pushed up and down with a thumb of a hand of a user who grasps the operation portion, and to vary a position of the monitor of the device main body to a desired angled position which faces the user straight.

17. The display device according to claim 16, wherein the tilt lever is provided with a switch for performing various functional operations.

18. The display device according to claim 16, wherein the protruding surface is formed by a plane.

19. The display device according to claim 16, wherein the protruding surface is formed by a curved surface along an extending direction.

20. The display device according to claim 16, wherein the protruding surface is formed by a plurality of surfaces.

21. The display device according to claim 16, wherein
the tilt lever includes a finger-hooking surface on which a user hooks a finger to operate to rotationally move the device main body, the finger-hooking surface being disposed continuously from the protruding surface; and
the finger-hooking surface includes a plurality of convex portions.

* * * * *